US010835292B2

(12) United States Patent
Hammann et al.

(10) Patent No.: US 10,835,292 B2
(45) Date of Patent: Nov. 17, 2020

(54) RIB FIXATION DEVICE AND RELATED METHODS

(71) Applicant: NuVasive, Inc., San Diego, CA (US)

(72) Inventors: Conrad Tyler Hammann, San Diego, CA (US); Prakhar Goel, San Diego, CA (US); Scott Lish, San Diego, CA (US); Fernando Olea, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 16/007,834

(22) Filed: Jun. 13, 2018

(65) Prior Publication Data

US 2019/0380745 A1    Dec. 19, 2019

(51) Int. Cl.
*A61B 17/70* (2006.01)

(52) U.S. Cl.
CPC ...... *A61B 17/7046* (2013.01); *A61B 17/7032* (2013.01); *A61B 17/7056* (2013.01); *A61B 17/7059* (2013.01)

(58) Field of Classification Search
CPC ............ A61B 17/7046; A61B 17/7085; A61B 17/7086; A61B 17/7091; A61B 17/7011; A61B 17/7032; A61B 17/7034; A61B 17/7049; A61B 17/7059; A61B 17/7056; A61B 17/7014; A61B 17/7004; A61B 17/7031; A61B 17/705; A61B 17/707; A61B 17/7055; A61B 17/7002; A61B 17/7052; A61B 17/8695
USPC .......................... 606/86 A, 246–279, 300–328
See application file for complete search history.

(56) References Cited

U.S. PATENT DOCUMENTS

| | | | |
|---|---|---|---|
| 5,092,889 A | 3/1992 | Campbell, Jr. | |
| 5,261,908 A | 11/1993 | Campbell, Jr. | |
| 5,334,203 A * | 8/1994 | Wagner ............. | A61B 17/7052 24/396 |
| 5,632,744 A | 5/1997 | Campbell, Jr. | |
| 5,800,434 A | 9/1998 | Campbell, Jr. | |
| 6,176,861 B1 * | 1/2001 | Bernstein ........... | A61B 17/7007 606/246 |
| 6,709,435 B2 * | 3/2004 | Lin ..................... | A61B 17/7001 606/250 |
| 6,860,884 B2 * | 3/2005 | Shirado ............. | A61B 17/7022 606/330 |
| 6,918,910 B2 | 7/2005 | Smith et al. | |

(Continued)

FOREIGN PATENT DOCUMENTS

| | | |
|---|---|---|
| CA | 2451977 | 11/1993 |
| CA | 2452127 | 12/1993 |

(Continued)

OTHER PUBLICATIONS

US 9,161,784 B2, 10/2015, Buttermann (withdrawn)

*Primary Examiner* — Pedro Philogene

(57) ABSTRACT

A rib fixation plate is provided that is can have one or more locking rib hooks that can translate and rotate independently from one another. The one or more locking rib hooks translate and rotate when in an unlocked conformation and are secured from translation and rotation when in a locked conformation. The plate includes a first end and a second end opposite of the first end, the second end having a housing assembly configured to receive a rod. The rod can be secured to a vertebra with a pedicle screw.

20 Claims, 8 Drawing Sheets

(56) References Cited

U.S. PATENT DOCUMENTS

| | | |
|---|---|---|
| 7,029,472 B1 | 4/2006 | Fortin |
| 8,016,837 B2 | 9/2011 | Giger et al. |
| 8,177,823 B2 * | 5/2012 | Lake .................. A61B 17/7056 606/276 |
| 8,236,002 B2 | 8/2012 | Fortin et al. |
| 8,298,240 B2 | 10/2012 | Giger et al. |
| 8,568,457 B2 | 10/2013 | Hunziker |
| 8,790,380 B2 | 7/2014 | Buttermann |
| 8,808,328 B2 | 8/2014 | Hwang |
| 8,894,663 B2 | 11/2014 | Giger et al. |
| 8,956,392 B2 | 2/2015 | Khatchadourian et al. |
| 8,974,500 B2 | 3/2015 | Khatchadourian et al. |
| 9,168,068 B2 * | 10/2015 | McClintock ....... A61B 17/7032 |
| 9,168,151 B2 * | 10/2015 | Sweeney ............ A61B 17/1671 |
| 9,204,899 B2 | 12/2015 | Buttermann |
| 9,204,908 B2 | 12/2015 | Buttermann |
| 9,282,997 B2 | 3/2016 | Hunziker |
| 9,314,285 B2 | 4/2016 | Reisberg |
| 10,206,718 B1 * | 2/2019 | Di Lauro ........... A61B 17/7032 |
| 2005/0234448 A1 | 10/2005 | McCarthy |
| 2008/0051784 A1 | 2/2008 | Gollogly |
| 2010/0004697 A1 | 1/2010 | Fortin et al. |
| 2010/0280519 A1 | 11/2010 | Soubeiran |
| 2013/0150889 A1 | 6/2013 | Fening et al. |
| 2014/0222074 A1 | 8/2014 | Rathbun et al. |
| 2014/0277147 A1 | 9/2014 | Alexander et al. |
| 2014/0296918 A1 | 10/2014 | Fening et al. |
| 2014/0364911 A1 | 12/2014 | Hwang |
| 2015/0134002 A1 | 5/2015 | Khatchadourian et al. |
| 2015/0190174 A1 | 7/2015 | McCarthy et al. |
| 2015/0190178 A1 * | 7/2015 | McCarthy .......... A61B 17/7049 606/276 |
| 2016/0030088 A1 | 2/2016 | Lim et al. |
| 2017/0238969 A1 * | 8/2017 | Sylvia ................ A61B 17/7011 |

FOREIGN PATENT DOCUMENTS

| | | |
|---|---|---|
| CN | 103767778 | 5/2014 |
| DE | 202012012881 | 5/2014 |
| FR | 2891726 | 4/2007 |
| FR | 2900563 | 11/2007 |
| SU | 1106486 | 8/1984 |
| WO | WO1993022989 | 11/1993 |
| WO | WO2007051924 | 5/2007 |

* cited by examiner

RIB FIXATION DEVICE AND RELATED METHODS

BACKGROUND

Field

The present disclosure relates generally to medical devices, and specifically to bone fixation instruments and methods for performing surgical procedures.

Background

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Surgical procedures on the spine often include the immobilization of one or more vertebrae. Immobilizing the vertebrae may be accomplished in many ways (e.g. fixation plates and pedicle screw systems). One of the most common methods for achieving the desired immobilization is through the application of bone anchors (most often introduced into the pedicles associated with the respective vertebrae to be fixed) that are then connected by rigid rods locked to each pedicle screw. These pedicle screw systems are very effective. However, vertebrae of pediatric patients can be small, making the use of pedicle screws challenging, and the vertebrae of trauma patients, or patients having decreased vertebrae strength, may not have sufficient bone structure with which to use pedicle screw systems. Moreover, bone structures of patients vary in size and location based on that particular patient's anatomical profile, accounting for physiological characteristics such as patient age and patient size. Therefore, a need continues to exist for new bone fixation devices that can be used as alternatives to pedicle screws and that are also adjustable to use with a wide variety of patients having different physiological characteristics.

SUMMARY

The present disclosure describes a rib fixation plate, including parts thereof, useful for securing, for example, a spinal rod in multiple spinal surgery techniques. The plate can be used with a rib hook that can translate across the plate. The rib hooks can also rotate around an axis with the plate. The modifiable nature of the rib hooks with the plate confers flexibility to the plate in the types of procedures for which it can be used, and allows a surgeon to alter the configuration of the rib hook during a procedure as necessary. The rib hook includes a locking element such that the surgeon can lock the rib hook in a secured position when the rib hook is in a desired lateral and rotational position.

In a first aspect, a plate for securing a spinal rod to a rib bone is provided, the plate comprising: an elongate body including a first end and a second end opposite of the first end, the first end being configured to be secured to a rod; an aperture formed in the body, the aperture disposed along an axis extending from the first end to the second end; and a first locking rib hook configured to receive at least part of a rib bone. The first locking rib hook is disposed within the aperture and configured to translate within the aperture when the first locking rib hook is in an unlocked conformation. The first locking rib hook is configured to be locked against translating within the aperture when in a locked conformation.

In a second aspect, a kit is provided for securing one or more bones of a subject, comprising: a plate including first end and a second end, a track extending from the first end to the second end, and a rod housing. The kit includes a first locking rib hook configured to receive at least part of a rib bone, and which is configured to slidably engage the track. The kit includes a rod configured to be secured in the rod housing, and a pedicle screw configured to secure the rod to a bone of the subject.

In a third aspect, a rib fixation plate assembly is provided. The rib fixation plate assembly comprises: a plate including a first end and a second end, a track extending from the first end to the second end, and a rod housing; a locking rib hook dimensioned to receive a rib bone of a subject, the locking rib hook positioned in the track, wherein the locking rib hook is configured to translate within the track when the locking rib hook is in an unlocked conformation, and wherein the locking rib hook is configured to be secured with the track when the locking rib hook is in a locked conformation; a rod secured with the rod housing; and a pedicle screw disposed on the rod and configured to secure the rod to a bone of the subject. An alternative embodiment of the rib fixation plate is also contemplated, wherein the plate includes an integrated rod extending therefrom instead of a rod housing to receive a separate rod. According to another contemplated alternative embodiment, the plate includes a lamina hook instead of a rod housing, rod and pedicle screw.

In a fourth aspect, a method of securing a spinal rod to a rib bone is provided. The method comprises: positioning a rib hook of the plate of the first aspect at least partially around a rib of a subject while in the unlocked conformation; locking the rib hook in the aperture; anchoring a bone anchor to a vertebral structure of the subject; and securing the rod to the bone anchor and the rib plate.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Figure 1:
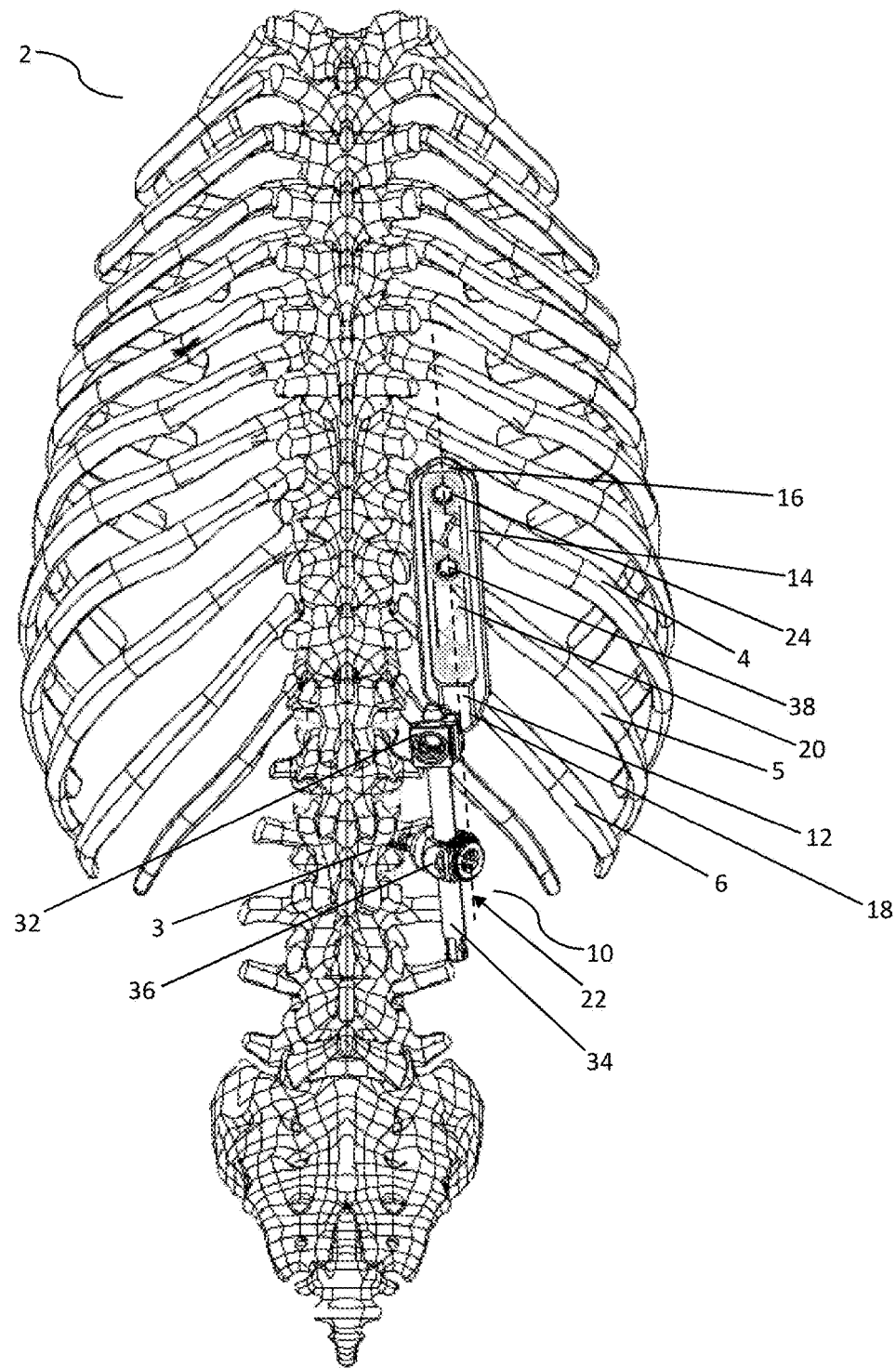
FIG. 1. An anterior view of an embodiment of a rib fixation assembly after placement with a rib bone and a vertebra.
Figure 2:
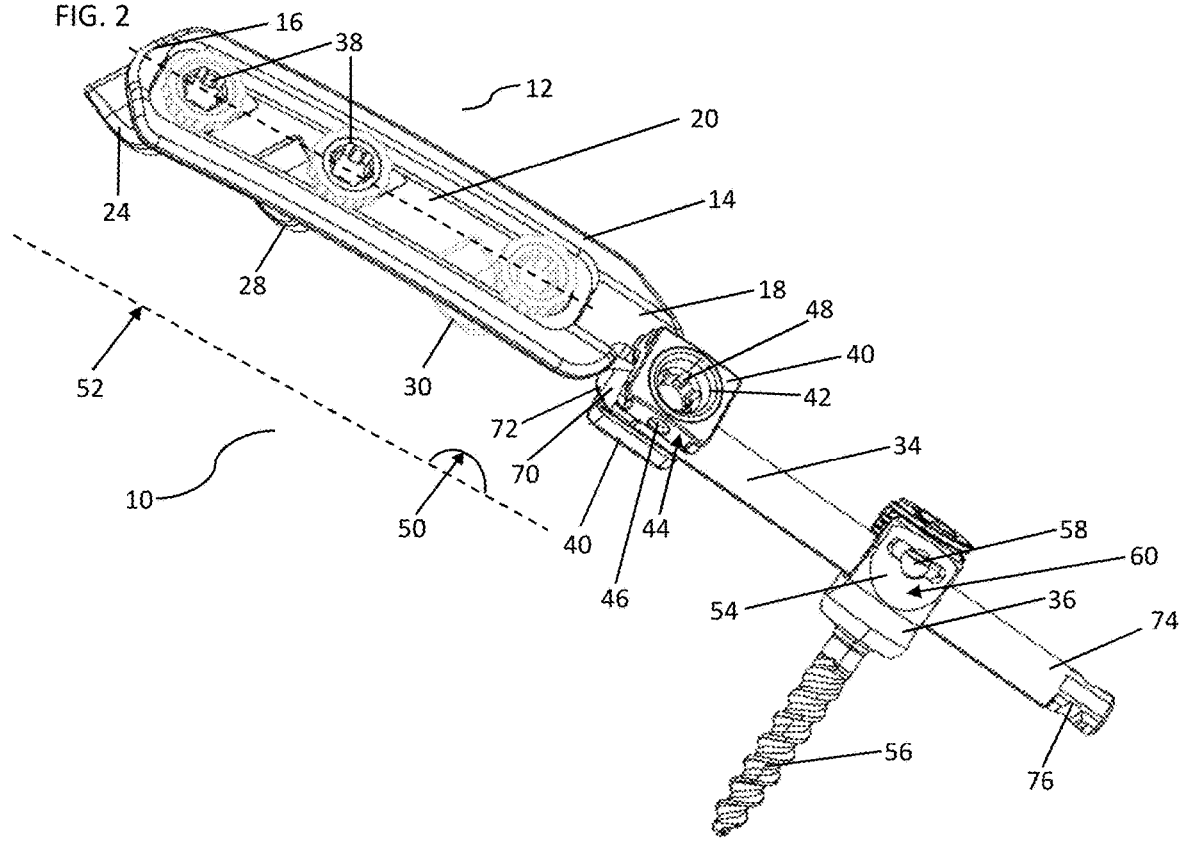
FIG. 2. A perspective view of the embodiment of the assembly of FIG. 1.
Figure 3:
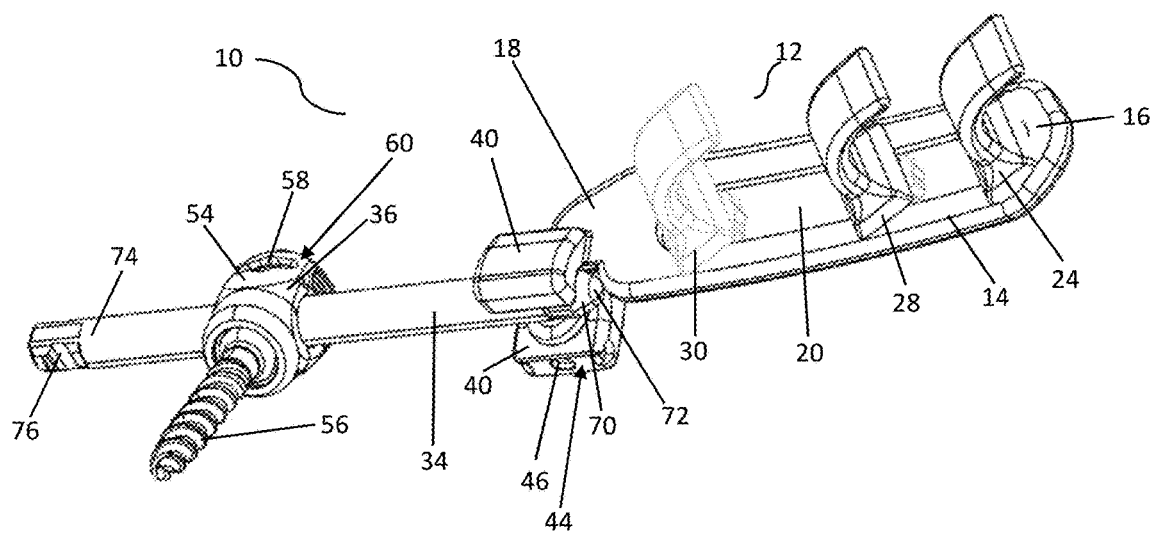
FIG. 3. An alternate perspective view of the embodiment of the assembly of FIG. 1.
Figure 4:
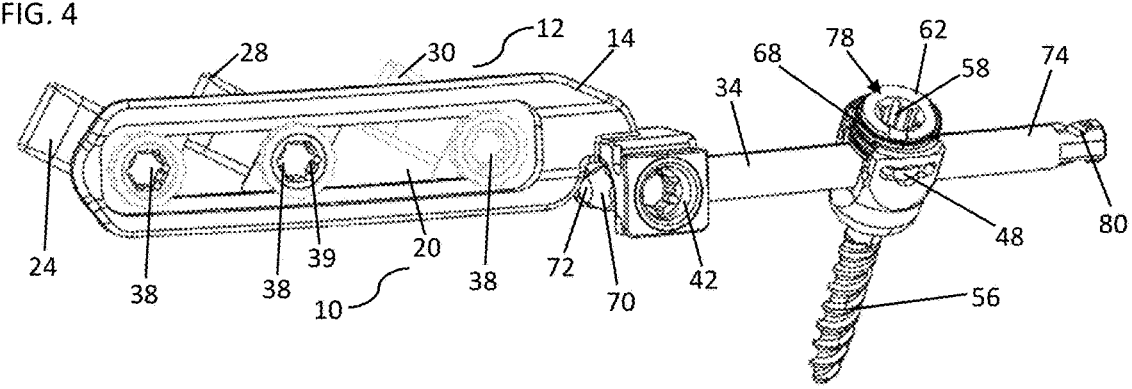
FIG. 4. An elevation view of the embodiment of the assembly of FIG. 1.

Illustrative embodiments of a rib fixation plate are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The rib fixation plate disclosed herein boasts a variety of inventive features and components that warrant patent protection, both individually and in combination.

The overall configuration of an illustrative embodiment of the rib fixation plate assembly 10 is shown in FIGS. 1-6. In this embodiment of the assembly 10, a plate 12 includes a body 14 having a first end 16 (e.g., cranial) and a second end 18 (e.g., caudal) opposite of the first end 16. The body 14 may be elongated from the first end 16 to the second end 18. An aperture, or track, 20 may be disposed within, such as by being integrally formed with, the body 14. The aperture 20 may extend in an axis 22 extending from the first end 16 to the second end 18. A first locking rib hook 24 may be disposed within the aperture 20. The first locking rib hook 24 may be configured, or dimensioned, to receive at least part of a subject's 2 rib bone 4. The first locking rib hook 24 may be configured to translate within the aperture 20 along the direction of the axis 22. Thus, the first locking rib hook 24 may be capable of translating between the first end 16 and the second end 18 of the body 14. Moreover, the first locking rib hook 24 may rotate around a first hook axis 26 (shown in FIG. 5). Advantageously, a surgeon can adjust, by translating and/or rotating, the first locking rib hook 24 within the plate 12 to fit the anatomical characteristics of the subject 2. This feature also allows the surgeon more flexibility in placing the plate 12 within the subject 2. A further benefit of the disclosed embodiments is that the rib hook may be moved and rotated to be usable with different patient types, such as subjects 2 of varying age (children and adults) and subjects 2 who have had trauma to one or more rib bones, as well as unique anatomical characteristics of subjects 2 (varying rib bone shape, varying rib bone size, etc.).

Figure 5:
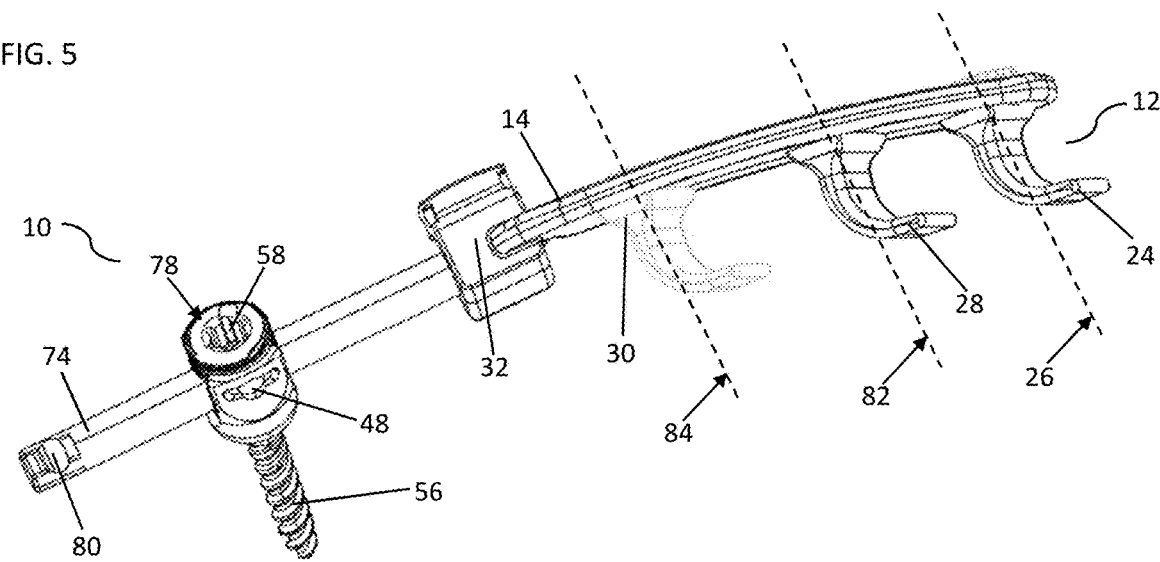
FIG. 5. Another view of the embodiment of the assembly of FIG. 1.

As can be seen in FIG. 1, the assembly 10 may include multiple locking rib hooks, each similar to the first locking rib hook 24. The illustrated embodiment shown in this embodiment of the assembly 10 has the first locking rib hook 24, a second locking rib hook 28, and a third locking rib hook 30, each of which are configured to receive at least part of the first rib bone 4, second rib bone 5, and third rib bone 6, respectively. A benefit to this embodiment of the assembly 10 is that each rib hook 24, 28, 30 may be translated within the aperture 20, and each rib hook 24, 28, and 30 may be rotated along a respective first hook axis 26, second hook axis 82, and third hook axis 84 (as shown in FIG. 5). It is appreciated that embodiments of the assembly 10 may comprise one locking hook, two locking hooks, or more than three locking hooks (i.e., four hooks, five hooks, etc.) (not shown).

A benefit of embodiments of the assembly 10 having two or more locking hooks is that the plate 12 has additional stability against movement, including yaw, pitch, and roll. Yet another benefit this embodiments of the assembly 10 having multiple locking hooks is that each locking hook may be adjusted individually to cooperate with the rib bones of the subject 2. For example, the locking hooks may be individually translated to account for varying intercostal space (i.e., the space between two ribs) between adult and child subjects 2. Thus, the hooks may be adjusted regardless of whether the subject 2 is in an adult having a typical adult intercostal space height or a child having an intercostal space height typical of a child of that age. Furthermore, each rib hook may be individually rotated along its respective hook axis to cooperate with each rib it is configured to receive.

The plate 12 may include a rod housing 32 configured to receive a rod 34. The rod housing 32 may be disposed at any point along the plate, such as at the second end 18 of the plate 12 as shown in the illustrated embodiments. The rod 32 may be variously secured within the rod housing 32. A pedicle screw 36 may be disposed elsewhere on the rod 34 to secure the rod to a vertebra 3 of the subject 2. Advantageously, in this embodiment, the pedicle screw 36 is configured to secure a bone 3 (e.g., a spinal pedicle as shown in FIG. 1) that is desired to be immobilized without needing an additional pedicle screw to another vertebra. While a second, third, etc. pedicle screw could be used with the assembly 10, they are not required as the plate 12 provides support to the assembly 10, which is particularly beneficial in child subjects 2, subjects suffering from decalcification, and subjects who have had spinal trauma 10, as these subjects 2 often lack vertebrae that can adequately support a pedicle screw. Further, the plate 12 may be bendable to provide varying curvature to accommodate the specific rib cage curvature of individual patients.

As described in further detail below, the assembly 10 may include a hook locking element 38 configured to transition each locking rib hook 24, 28, 30 between an unlocked conformation and a locked conformation. The locking rib hooks 24, 28, and 30 are shown in FIG. 1 a locked position each secured to the respective first rib bone 4, second rib bone 5, and third rib bone 6, and are secured against translation and rotation.

FIGS. 2-6 illustrate the assembly 10 isolated from a subject 2. The assembly 10 has the first, second, and third locking rib hooks 24, 28, 30 disposed at least partially within the track 20. Each of the first, second, and third locking ribs 24, 28, 30 may have the hook locking element 38. The rod housing 32 in the illustrated embodiment is disposed on the second end 18. The rod housing 32 may comprise a pair of arms 40 configured to receive the rod 34 at least partly therein. The pair of arms 40 may be integrally formed with the body 14 of the plate 12. The rod housing 32 may include a threaded aperture (not shown) for receiving a rod locking element 42, such as a locking screw, to secure the rod in a desired position with the plate 12. A surface 44 of rod housing 32 may include a tool engagement feature 46 for inserting and rod housing 32 during a surgical procedure. The locking element 42 may include an instrument engagement feature 48 for locking the locking element 42 with an instrument (not shown), such as a driver for reducing a locking screw. While not shown, the locking element 38 may include a threads which cooperate with a surface of the rod housing 32 having cooperative threads for receiving and locking the locking element 42. The rod housing 32 may allow for a rod to be adjusted, such as an angle 50 of the plate 12 and the rod 34 in an axis 52 parallel to the axis 22. As illustrated, the angle 50 is 180 degrees, but may be adjusted, for example, between 90 and 270 degrees, between 120 and 240 degrees, between 150 and 210 degrees, between 170 and 190 degrees, between 175 and 185 degrees, or any combination of ranges thereof.

The pedicle screw 36 may be anchored to a vertebral structure and then secured to the rod 34. The pedicle screw 34 may have a tulip shape profile, having a pair of arms 54 extending oppositely from a screw portion 56. The screw portion may have external threads disposed thereon configured to be secured within a pedicle of the vertebra 2. The rod 34 may be disposed between the pair of arms 54. The pair of arms 54 may each, or both, have a tool engagement feature 58 disposed on an external surface 60 of the pair of arms 54 such that the pedicle screw may be inserted and positioned during a surgical procedure. The pair of arms 54 may be configured to receive a locking element 62, such as a locking screw. The pair of arms 54 may have an interior surface 64 having threads 66 (shown in FIG. 13) configured to cooperatively engage with threads 68 on the locking element 62. The interior surface 64 may have a profile complementary to the rod 34 such that rod 34 is secured when the locking element 62 is in a locked conformation (e.g., the rod 34 is reduced and secured with the locking element). The locking element 62 may have a surface 78 facing away from the rod 34, the surface 78 having a tool engagement element 80 disposed thereon for engaging a tool, such as a driver (not shown) for securing the pedicle locking element 62 with the rod 34 (e.g., reducing the rod).

The locking rib hooks 24, 28, and 30 are configured to independently translate within the aperture 20 and independently rotate around the first hook axis 26, a second hook axis 82, and a third hook axis 84, respectively. The hooks 24, 28, and 30 rotate relative to the body 14 of the plate 12 such that they can be in various positions independently of one another. When in a locked conformation, the locking rib hooks 24, 28, and 30 are secured from translation within the aperture 20 and secured from rotation around the first, second, and third hook axis 26, 82, and 84, respectively. Thus, the first hook 24 may be rotated and translated so as to receive a caudal part of the first rib bone 4, while the second hook 28 may be in translated and in a generally opposing position so as to receive a cranial part of the second rib bone 5. This customizability of the location and orientation of the rib hooks 24, 28, and 30 enables the surgeon to adjust the rib hooks 24, 28, and 30 for each patient and surgical procedure.

Figure 7:
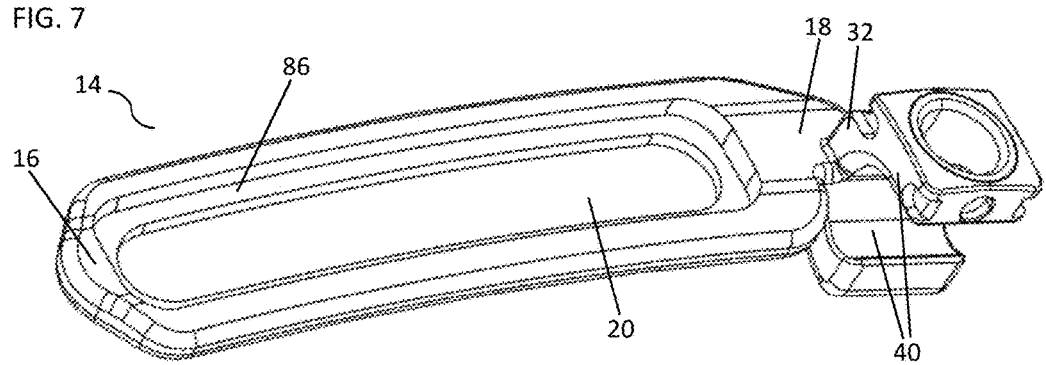
FIG. 7. A perspective view of a body of a plate of FIG. 1.
Figure 8:
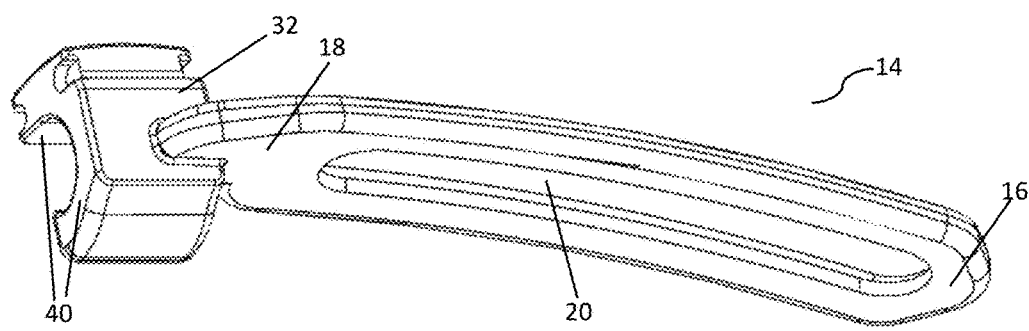
FIG. 8. Another perspective view of the body of FIG. 7.
Figure 9:
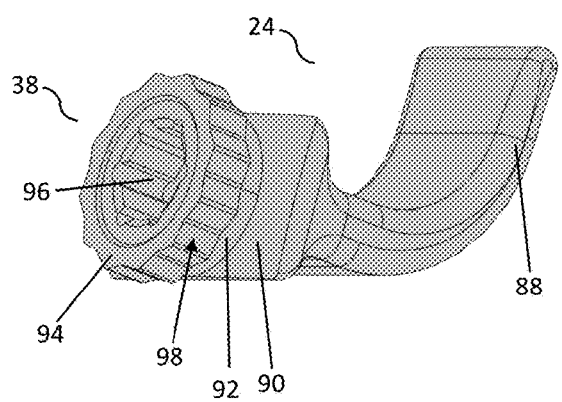
FIG. 9. A perspective view of a rib hook of the assembly of FIG. 1.
Figure 10:
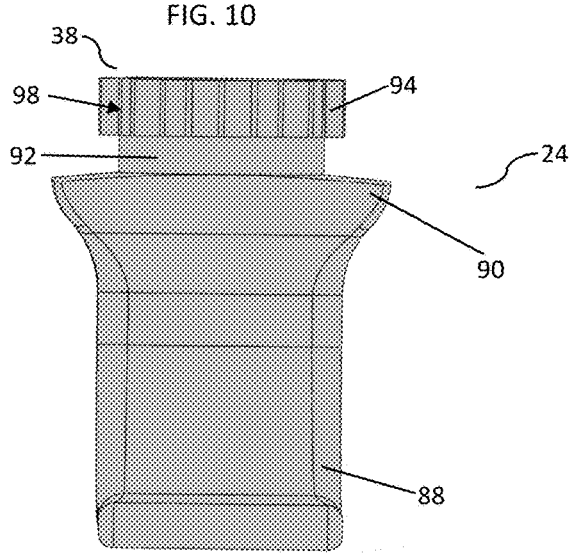
FIG. 10. A front elevation view of the rib hook of FIG. 9.
Figure 11:
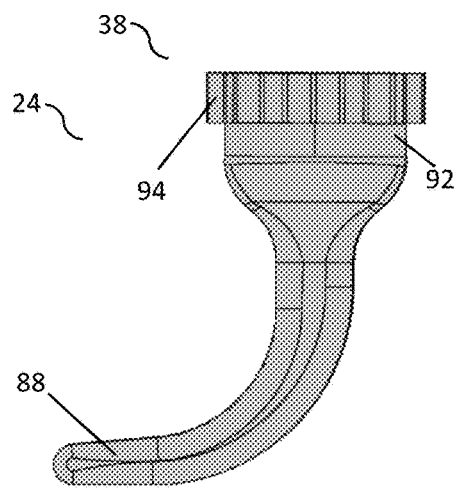
FIG. 11. A side view of the rib hook of FIG. 9.
Figure 12:
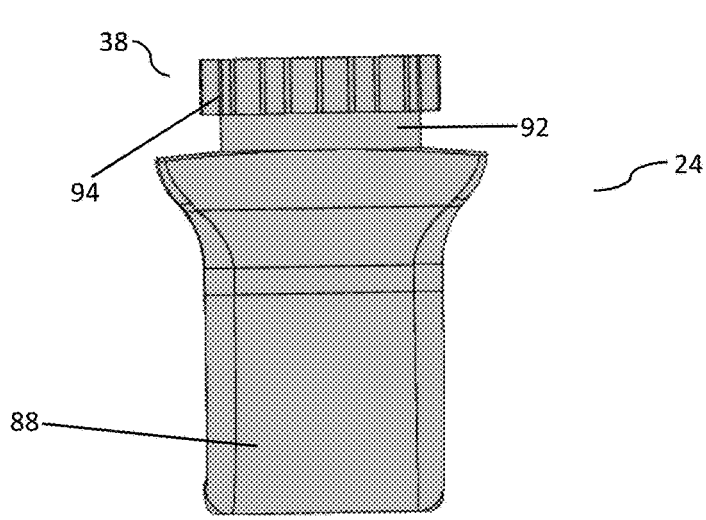
FIG. 12. A rear side view of the rib hook of FIG. 9.

Turning to FIGS. 7 and 8, a plate 12 is illustrated with the rib hooks not shown. The aperture or track 20 may include an indentation or shelf 86 configured to receive a rib hook. An embodiment of first rib hook 24 is illustrated in FIGS. 9-12. Again, the second rib hook 28, the third rib hook 30, or any other additional rib hook, may be of the same design or construction as the rib hook 24. The first rib hook includes a curved arm 88 for receiving a rib bone extending from a base 90. The base 90 may be configured to be slidingly and cooperatively received within indentation or shelf 86. The hook locking element 38 of the first hook 24 may include a post 92 extending from the base 90 oppositely from the arm 88. The post 92 may have threads disposed thereon (not shown) for receiving a nut 94 having corresponding cooperating threads (not shown). The nut may have an outer contour 96 that is engageable by a driver tool for transitioning the hook locking element 38 between a locked conformation and an unlocked conformation. The hook post 92 may include a tool engagement element 39 configured to facilitate the translation and/or rotation of the hook 24, 28, 30 in the track using one or more surgical tools. The nut 94 may have a gripper external surface 98 configured for receiving a gripping tool or to be tightened by hand by the surgeon during a surgical procedure (not shown).

In an embodiment (not shown), the base 90 of the first locking rib hook 24 includes a channel disposed therein for receiving the hook locking element 38. The channel within the base 90 may include interior threads (not shown) for cooperatively receiving corresponding threads on the locking element 38.

Figure 6:
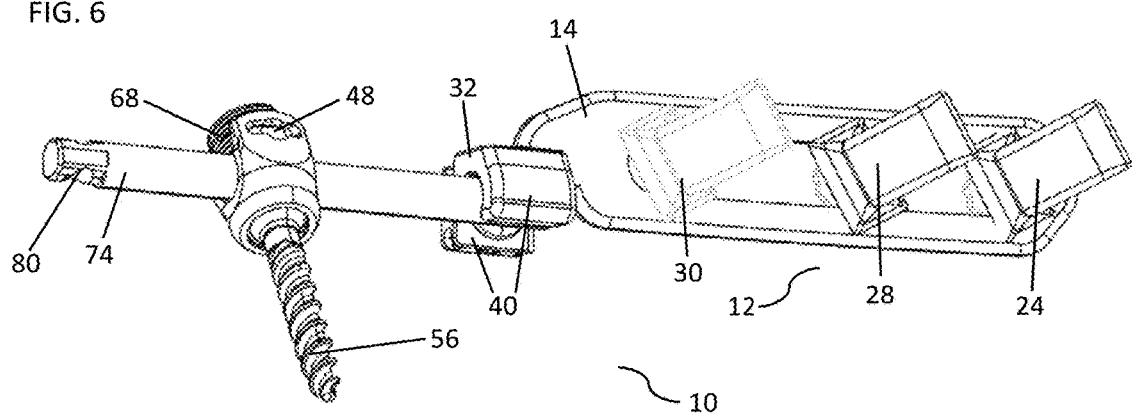
FIG. 6. Yet a further perspective view of the embodiment of the assembly of FIG. 1.
Figure 13:
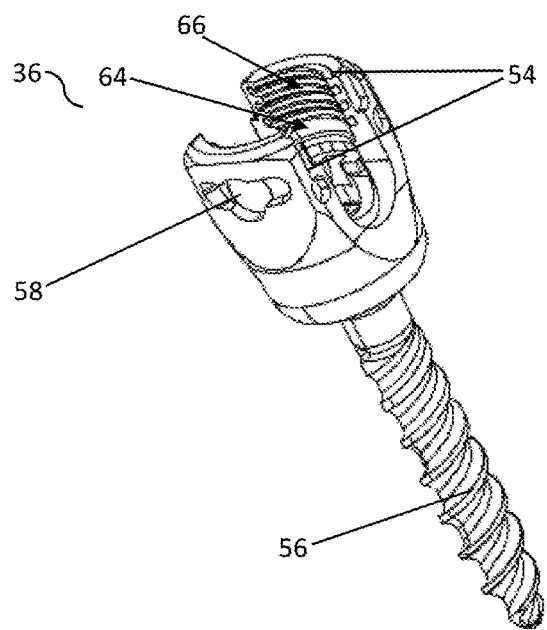
FIG. 13. A perspective view of a pedicle screw of the assembly of FIG. 1.
Figure 14:
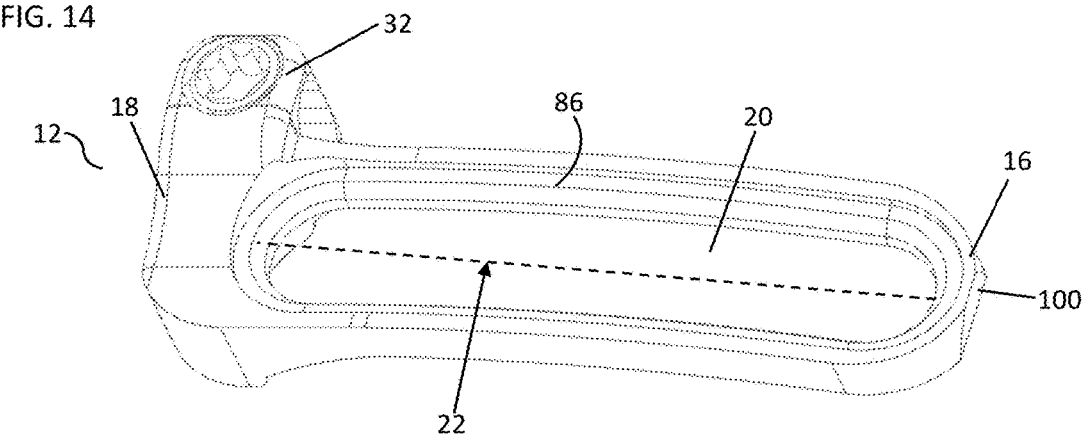
FIG. 14. A perspective view of an embodiment of a body of a retractor plate.
Figure 15:
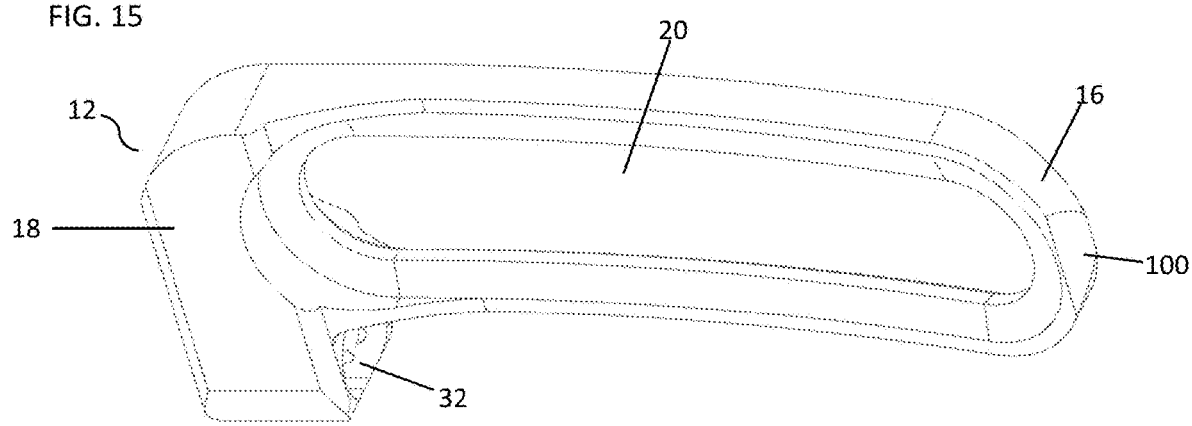
FIG. 15. Another perspective view of the embodiment of the body of FIG. 14.
Figure 16:
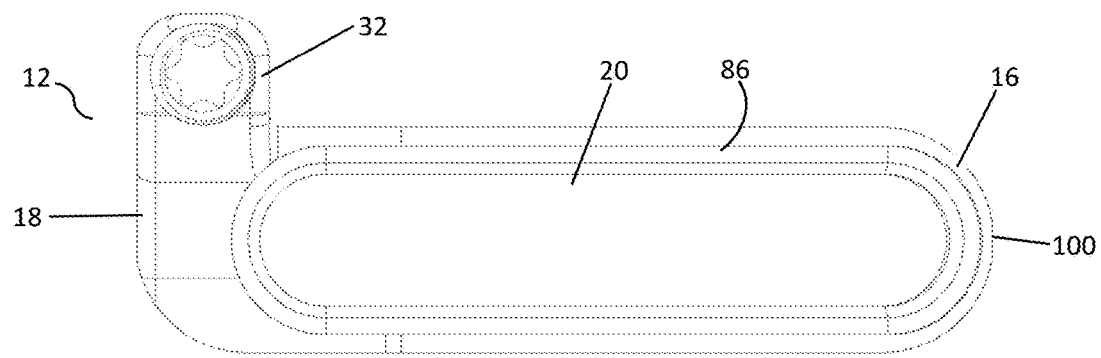
FIG. 16. A top view of the embodiment of the body of FIG. 14.
Figure 17:
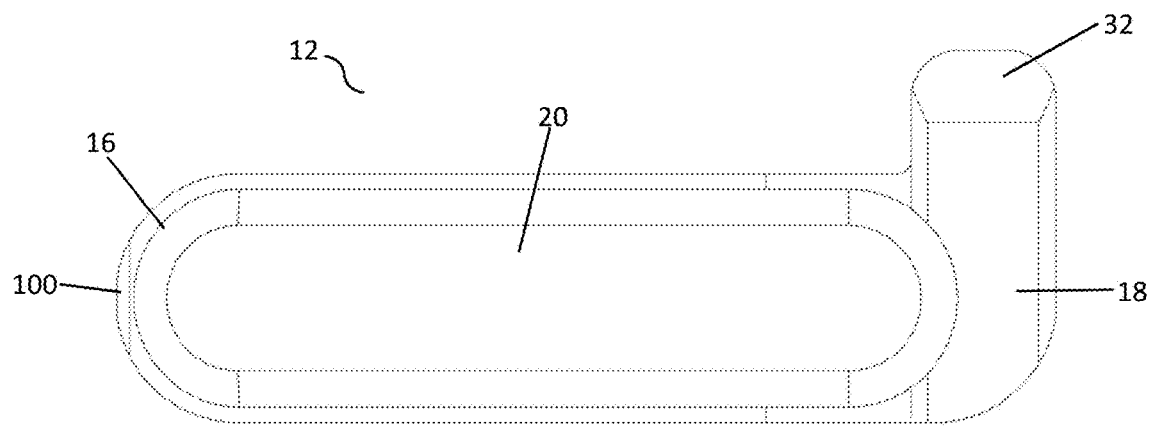
FIG. 17. A bottom view of the embodiment of the body of FIG. 14.
Figure 18:
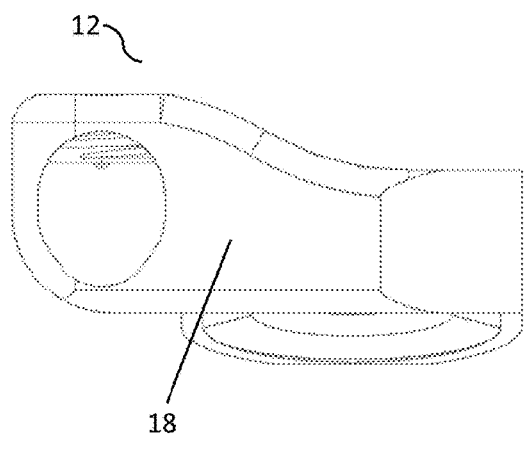
FIG. 18. A left side view of the embodiment of the body of FIG. 14.
Figure 19:
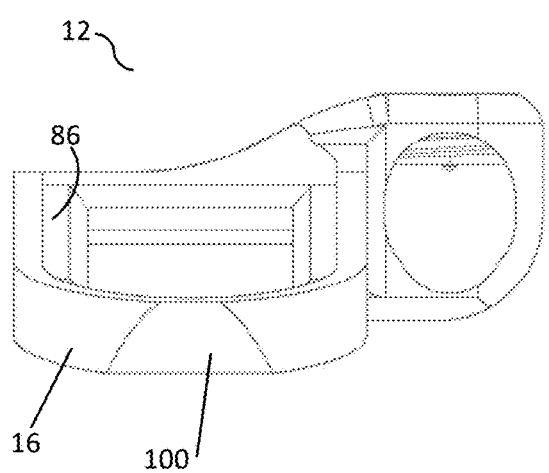
FIG. 19. A right side view of the embodiment of the body of FIG. 14.

FIG. 13 illustrates a detailed view of an embodiment of a pedicle screw 36 having a tulip profile, with the screw portion 56 extending oppositely from the pair of arms 54. The pair of arms 54 have an interior surface 64 having threads 66 that correspond with the threads 68 of the pedicle locking element 62 (as shown in FIG. 6) such that, for example, the pedicle locking element 62 may be used to reduce the rod 34 (FIG. 6) within the arms 54. The pedicle screw 36 has an external surface 60 having a tool engagement feature 68 for inserting and positioning the pedicle screw 36.

Figure 20:
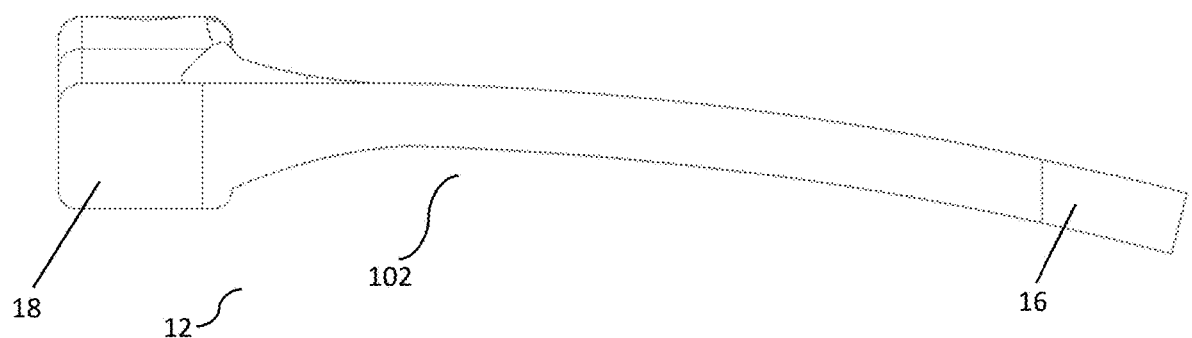
FIG. 20. A front elevation view of the embodiment of the body of FIG. 14.
Figure 21:
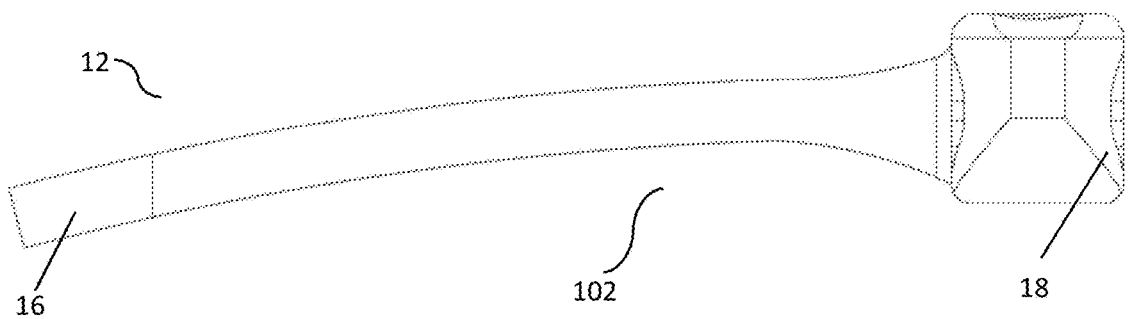
FIG. 21. A rear elevation view of the embodiment of the body of FIG. 14.

FIGS. 14-21 illustrate an embodiment of the plate 12 having a radiused profile 102 from the second end 18 to the first end 16, as best illustrated in FIGS. 20 and 21. The plate 12 has the indentation/shelf 86 formed therein shaped complimentary to the base 90 of a rib hook 24, 26, 30 and configured to enable the rib hook 24, 26, 30 to move along the axis 22 of the aperture 20. The first end 16 may have a notch 100 formed therein, and the second end 18 may have the rod housing 32 adjacently extending therefrom in a direction perpendicular to the axis 22.

Kits for securing one or more bones of a subject are provided herein employing pieces of the assembly 10, comprising the plate 12 including the first end 16 and the second end 18, a track 20 extending from the first end 16 to the second end 18, and the rod housing 32. The kit may include a first locking rib hook 24 configured to receive at least part of the first rib bone 4, the first locking rib hook 24 configured to slidably engage the track 20. The kit may include the rod 34 configured to be secured in the rod housing 32. The kit may include a pedicle screw 36 configured to secure the rod 34 with a bone 2, such as a vertebra, of the subject 2. The kit 10 may include multiple hooks, such as the second locking rib hook 28, the third locking rib hook 30, or additional hooks. To emphasize, the second locking rib hook 28 and the third locking rib hook 30, or any additional hooks, may be the same as the first locking rib hook 24, such as being configured to slidably engage the track 20 and being configured to lock from translation and rotation with the hook locking element 38. The kit may include the locking element 62.

Surgical procedures are provided employing the plate 12, comprising securing the plate 12 to one or more bones during or after an incision. By way of example, a method of securing a bone is provided. The plate 12 is provided, wherein the first locking rib hook 24 is coupled with the track 20 of the plate 12 such that the first locking rib hook 24 is slidably engaged with the track 20. The first locking rib hook 24, the second locking rib hook 28, the third locking rib hook 30, or any combination thereof, may be rotated around a respective axis 26, 82, 84 perpendicular to the axis 22 extending from the first end 16 to the second end 18 to rationally engage the respective rib bone 4, 5, 6 as necessary to be properly oriented relative to the ribs. The first locking rib hook 24 is slid to engage the first rib bone 4. The first locking rib hook 24 is locked in place with the first rib bone and the plate 12 from translational and rotational movement. The second locking hook 28 may be coupled with the track 20. The second locking hook 28 is slid to engage the second rib bone 5. The second locking hook 28 is locked in place with the second rib bone and the plate 12 from translational and rotational movement. The third locking rib hook 30 may be similarly positioned and locked. A pedicle screw 36 configured to secure the spinal bone 3, such as a vertebra, may be engaged with the rod, after being secured to the spinal bone 3. The rod 34 may be secured in the rod housing 32 of the plate 12 and of the pedicle screw.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A plate, comprising:
   an elongate body including a first end and a second end opposite of the first end, wherein the second end is configured to be secured to a rod;
   an aperture formed in the body disposed along a longitudinal axis of the elongate body;
   a rod housing longitudinally extending from the second end of the elongate body, and comprising an arm with an aperture for receiving a locking element therewithin, the arm extending beyond a top surface running from the first end to the second end of the elongate body; and
   a first locking rib hook configured to receive at least part of a rib bone, the first locking rib hook disposed within the aperture and configured to translate within the aperture when the first locking rib hook is in an unlocked conformation, and wherein the first locking rib hook is configured to be locked against translating within the aperture when in a locked conformation, wherein the first locking rib hook comprises a threaded post and wherein a locking element is threadedly engaged to an outer surface of the threaded post.

2. The plate of claim 1, wherein the locking element is configured to transition the first rib hook between the unlocked conformation to the locked conformation.

3. The plate of claim 2, wherein the locking element is a locking nut.

4. The plate of claim 1, wherein the post includes a tool engagement element configured to allow rotation of the locking element by a driver tool.

5. The plate of claim 1, wherein the first locking rib hook is configured to rotate about an axis perpendicular to the axis extending from the first end to the second end when the first locking rib hook is in the unlocked conformation.

6. The plate of claim 1, wherein the first locking rib hook is configured to be locked against rotating about an axis perpendicular to the axis extending from the first end to the second end when the first locking rib hook is in the locked conformation.

7. The plate of claim 1, further comprising a second locking rib hook configured to receive at least part of a rib bone, the second locking rib hook disposed within the aperture and configured to translate within the aperture when the second locking rib hook is in an unlocked conformation, and wherein the second locking rib hook is configured to be locked against translating within the aperture when in a locked conformation.

8. The plate of claim 7, wherein the second locking rib hook comprises a locking element configured to transition the second rib hook between the unlocked conformation to the locked conformation.

9. The plate of claim 8, wherein the second rib hook includes a threaded post and the second locking element is a locking nut threadedly engaged to the post.

10. The plate of claim 8, wherein the locking element of the second rib hook includes a tool engagement element configured to allow rotation of the locking element by a driver tool.

11. The plate of claim 8, wherein the second locking rib hook is configured to rotate about an axis perpendicular to the axis extending from the first end to the second end when the first locking rib hook is in the unlocked conformation.

12. The plate of claim 8, wherein the second locking rib hook is configured to be locked against rotating about an axis perpendicular to the axis extending from the first end to the second end when the first locking rib hook is in the locked conformation.

13. The plate of claim 7, wherein the first locking rib hook and the second locking rib hook are configured to be translatable and rotatable independently of each other.

14. A kit for securing one or more bones of a subject, comprising:
a plate including a longitudinal axis extending from a first end to a second end;
a track extending from the first end to the second end;
a rod housing laterally extending from and integral to a side of the second end of the plate in a direction perpendicular to the longitudinal axis of the plate, the rod housing comprising an arm with an aperture configured to receive a locking element therewithin, the arm extending beyond a top surface running from the first end to the second end of the elongate body;
a first locking rib hook configured to receive at least part of a rib bone, wherein the first locking rib hook is configured to slidably engage the track;
a rod configured to be secured in the rod housing; and
a pedicle screw configured to secure the rod with a bone of the subject.

15. The kit of claim 14, further comprising a second locking rib hook configured to receive at least part of a rib bone, wherein the second locking rib hook is configured to slidably engage the track.

16. The kit of claim 14, further comprising a hook locking element configured to lock the first locking rib hook with the plate, wherein the first locking rib hook comprises a threaded post and the hook locking element is threadedly engaged to an outer surface of the threaded post.

17. The kit of claim 14, further comprising a pedicle locking element configured to lock the pedicle screw with the rod.

18. A rib fixation plate assembly, comprising:
a plate including a longitudinal axis extending from a first end to a second end;
a track extending from the first end to the second end;
a rod housing laterally extending from and integral to a side of the second end of the plate in a direction perpendicular to the longitudinal axis of the plate, the rod housing comprising an arm with an aperture configured to receive a locking element therewithin, the arm extending beyond a top surface running from the first end to the second end of the elongate body;
a locking rib hook dimensioned to receive a rib bone of a subject, the locking rib hook received in the track, wherein the locking rib hook is configured to translate within the track when the locking rib hook is in an unlocked conformation, and wherein the locking rib hook is configured to be secured with the track when the locking rib hook is in a locked conformation;
a rod secured with the rod housing; and
a pedicle screw disposed on the rod and configured to secure the rod to a bone of the subject.

19. The rib fixation plate assembly of claim 18, wherein the plate and the rod are configured to rotate relative to one another around an axis when the rod is in an unlocked conformation, and wherein the plate and the rod are configured to be rotationally secured to one another around the axis when the rod is in a locked conformation.

20. The rib fixation plate assembly of claim 18, wherein the locking rib hook comprises a threaded post and a hook locking nut is threadedly engaged to an outer surface of the threaded post.

* * * * *